United States Patent [19]

Khandelwal et al.

[11] Patent Number: 5,206,241
[45] Date of Patent: Apr. 27, 1993

[54] LABDANES AND PROCESS FOR THEIR PREPARATION

[75] Inventors: Yatendra Khandelwal; Rajeshwari Kannan; Bansi Lal; Ramanujam Rajagopalan; Vijay A. Aroskar; deceased AliHussein N. Dohadwalla; Rashida A. Dohadwalla; Anis S. Dohadwalla; Samina A. Dohadwalla, all of Bombay, India, Heirs; Richard H. Rupp, Königstein/ Taunus, Fed. Rep. of Germany

[73] Assignee: Hoechst Aktiengesellschaft, Frankfurt am Main, Fed. Rep. of Germany

[21] Appl. No.: 669,685

[22] Filed: Mar. 14, 1991

[30] Foreign Application Priority Data

Mar. 17, 1990 [EP] European Pat. Off. ........ 90105072.4

[51] Int. Cl.$^5$ ................ A61K 31/535; A61K 31/495; A61K 31/445; A61K 31/35
[52] U.S. Cl. .................... 514/232.8; 514/255; 514/320; 514/455; 514/912; 544/150; 544/375; 546/196; 549/389
[58] Field of Search ................ 549/389; 514/455, 255, 514/232.8, 320; 546/196; 544/150, 375

[56] References Cited

U.S. PATENT DOCUMENTS

| | | | |
|---|---|---|---|
| 4,088,659 | 5/1978 | Bhat et al. | 424/283 |
| 4,118,508 | 10/1978 | Bhat et al. | 424/283 |

FOREIGN PATENT DOCUMENTS

| | | |
|---|---|---|
| 0193132 | 9/1986 | European Pat. Off. . |
| 2654786A1 | 6/1977 | Fed. Rep. of Germany . |
| 3346869A1 | 7/1984 | Fed. Rep. of Germany . |
| 3535086A1 | 4/1987 | Fed. Rep. of Germany . |
| 63242 | 8/1988 | India . |

OTHER PUBLICATIONS

Bhat, et al., "Reactions of Forskolin, a Biologically Active Diterpenoid from Coleus Forskohlii", Perkin Trans. 1, pp. 767-771 (1982).

Bhat, et al., "Structures and Stereochemistry of New Labdane Diterpenoids from Coleus Forskohlii Briq.", Tetrahedron Letters No. 19, Pergamon Press, pp. 1669-1672 (1977).

Khandelwal, et al., "Cardiovascular Effects of New Water-Soluble Derivatives of Forskolin", J. Med. Chem., vol. 31, pp. 1872-1879 (1988).

*Primary Examiner*—C. Warren Ivy
*Assistant Examiner*—A. A. Owens
*Attorney, Agent, or Firm*—Finnegan, Henderson, Farabow, Garrett & Dunner

[57] ABSTRACT

Labdanes of the formula

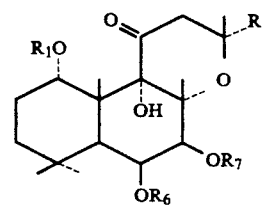

a process for their manufacture, pharmaceutical preparations containing an effective amount of these compounds and their use for the manufacture of a pharmaceutical preparation for treatment of cardiovascular diseases and high intraocular pressure.

8 Claims, No Drawings

LABDANES AND PROCESS FOR THEIR PREPARATION

This invention relates to novel pharmacologically active 6/7-acyloxy-7/6-aminoacyloxy-polyoxygenated labdane derivatives and a process for their preparation.

The following patents/patent applications and publications relate to polyoxygenated labdanes and their derivatives.

Indian patent No. 143 875 and the corresponding U.S. Pat. No. 4,088,659,

Indian patent No. 145 926,

Indian patent No. 147 030 and the corresponding U.S. Pat. No. 4,118,508,

Indian patent No. 147 007 and the corresponding German patent application No. P 26 54 786.6;

Tetrahedron Letters No. 19, pp. 1669-1672, 1977, J. Chem. Soc., Perkin Trans. 1, 767, 1982. Offenlegungsschrift DE 33 46 869;

Indian patent No. 163 242 and the corresponding German patent application No. P 35 35 086.5; J. Med. Chem. 31, 1872, 1988.

The pharmacological properties of polyoxygenated labdanes and their derivatives mentioned in the above prior art literature render them suitable for use in the treatment of cardiac and circulatory diseases, hypertension, glaucoma, allergy, broncho-constriction and as immunomodulators.

Examples of the polyoxygenated labdane derivatives of the present invention have not been cited in the earlier literature. Compounds of the prior art literature which are structurally related in part to the compounds of the invention are the derivatives which bear a 6-aminoacyloxy group in the polyoxygenated labdanes. The essential difference between the compounds of the invention and those of the prior art lies in the pattern of substitution at the 6- and 7-positions, namely in the compounds of the invention when one of the 6-substituent or 7-substituent is an aminoacyl group, the other is an alkoxyacyloxy or aryloxyacyloxy group, whereas in compounds of the prior art when the 6-substituent is an aminoacyloxy group, the 7-substituent is only either a hydroxy, acyloxy, or an aminoacyloxy group. This alteration in structure surprisingly alters the pharmacological profile of the compounds, which renders them potentially more useful especially for the treatment of glaucoma, and congestive cardiomyopathy, in contrast to compounds of the prior art.

Accordingly the object of the present invention is to provide novel pharmacologically active polyoxygenated labdane derivatives and a process for their preparation.

The present invention relates to labdanes of the formula I

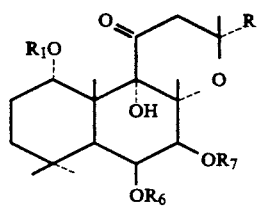

in which

R denotes vinyl, ethyl, cyclopropyl or CHOHCH$_2$OH,

R$_1$ denotes hydrogen, a group of the formula

A denoting OR$_2$, in which R$_2$ represents an alkyl group, or denoting

X and Y representing, if they are identical, hydrogen or alkyl, or, if X represents hydrogen or lower alkyl, Y representing an alkyl, substituted alkyl, cycloalkyl, aralkyl, aryl, amino or hydroxyl group, or X and Y, together with the nitrogen atom to which they are bonded, forming a heterocyclic ring which can contain a further hetero atom and can be substituted by an alkyl or aryl group, or R$_1$ may be represented by a group of the formula R$_3$R$_4$R$_5$Si, each of R$_3$, R$_4$ and R$_5$ independently denoting an alkyl group, R$_6$ or R$_7$ denotes a group of the formula

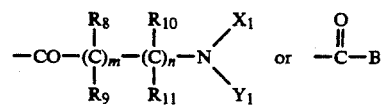

in which m and n are integers from 1 to 10, and R$_8$ and R$_9$ are identical or different and represent hydrogen or a lower alkyl group, or one of the substituents represents hydrogen and the other represents a hydroxyl, thio or aryl group, R$_{10}$ denotes hydrogen and R$_{11}$ denotes hydrogen or a hydroxyl or alkyl group, and X$_1$ represents hydrogen if Y$_1$ represents hydrogen, alkyl, substituted alkyl, alkanoyl, aryl, cycloalkyl, aralkyl, a heterocycle, amino, substituted amino, hydroxyl, acyl, dialkyl aminoalkyl, carbamoyl, carboxyalkyl or carbalkoxyalkyl, or X$_1$ and Y$_1$ represent, if they are identical, alkyl, substituted alkyl, aryl or aralkyl, or, if X$_1$ represents alkyl; Y$_1$ represents substituted alkyl, cycloalkyl, aralkyl or a dialkylaminoalkyl group, or X$_1$ and Y$_1$ form, together with the nitrogen atom to which they are bonded, a heterocycle which can contain one or more hetero atoms and be optionally substituted once or several times by alkyl, aryl, aralkyl, hydroxyalkyl, hydroxyl or other heterocyclic groups, and B denotes a substituted alkyl group with the proviso that R$_6$ and R$_7$ are not simultaneously

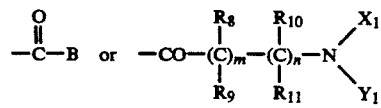

in which R$_8$ ro R$_{11}$, X$_1$, Y$_1$, m and n have the above meanings, and to their optical and geometric isomers and their pharmaceutically acceptable acid addition salts.

Preferred compounds of the formula I are those in which R has the above-mentioned meaning, preferably vinyl, $R_1$ represents hydrogen, $R_6$ represents a group of the formula

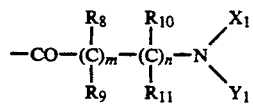

in which $R_8-R_{11}$, $X_1$ and $Y_1$ have the afore-mentioned meaning, and $R_7$ represents a group of the formula

wherein B has the above mentioned meaning.

Especially preferred are compounds of the formula I, wherein R is vinyl, $R_1$ is hydrogen, $R_6$ is a group of the formula

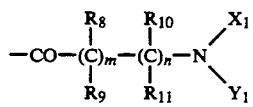

wherein m and n each are the integer 1, $R_8-R_{11}$ are hydrogen, $X_1$ and $Y_1$ are $C_1-C_4$-alkyl, preferably methyl or $X_1$ and $Y_1$ form together with the nitrogen atom to which they are bonded, a piperidine, morpholine or piperazine ring, which may be substituted by $C_1-C_4$-alkyl, preferably methyl, and $R_7$ is —CO—B. wherein B is $C_1-C_4$-alkyl, preferably methyl, substituted by $C_1-C_4$-alkoxy, phenoxy or halogeno-phenoxy.

The term alkyl relates to straight chain or branched saturated hydrocarbon radicals having 1 to 8 carbon atoms such as, for example, methyl, ethyl, propyl, 2-methylpropyl, 1-pentyl, 3-hexyl or 2-octyl and the like. Preferred alkyl groups have 1 to 6, in particular 1 to 4, carbon atoms. Especially preferred is methyl.

Suitable examples of substituted alkyl groups are hydroxyalkyl such as hydroxyethyl, carboxyalkyl such as carboxyethyl, carbalkoxyalkyl such as carboethoxyethyl, or halogenated alkyl. Alkoxyalkyl wherein alkoxy has 1–4 carbon atoms such as methoxymethyl or ethoxymethyl, aryloxyalkyl such as phenoxymethyl, halogenophenoxymethyl, such as p-chlorophenoxymethyl, aralkyl such as benzyl, thioalkyl such as methylthiomethyl. Especially preferred are methoxymethyl, ethoxymethyl, phenoxy- and p-chlorophenoxy. methyl.

Suitable cycloalkyl groups are $C_3-C_7$-cycloalkyl groups, in particular cyclopentyl or cyclohexyl.

An aralkyl group is to be understood to be a phenylalkyl group, preferably phenyl-$C_1-C_3$-alkyl, for example a benzyl group in which the phenyl group can be substituted once or several times by halogen, $C_1-C_3$-alkyl, $C_1-C_3$-alkoxy, nitro or trifluoromethyl.

An aryl group is to be understood to be a phenyl group which can be substituted once or several times by substitutents such as halogen, $C_1-C_3$-alkyl, $C_1-C_3$-alkoxy, nitro, amino, substituted amino or trifluoromethyl.

An acyl group is to be understood to be $C_1-C_6$-alkanoyl, $C_2-C_6$-alkenoyl, aroyl, aralkanoyl or heteroaroyl group having up to 10 carbon atoms, it being possible for one or more carbon atoms to be replaced by oxygen, nitrogen and/or sulfur.

Examples of alkanoyl groups are formyl, acetyl, propionyl, butyryl, isobutyryl, valeryl, palmityl and bromisobutyryl. The alkanoyl groups can contain one or more double bonds, for example an acryloyl, stearyl or oleoyl group. The alkanoyl groups can also contain one or more triple bonds as well as one or more double bonds. An example of alkynoyl group of this type is the propiolyl group. A representative of aroyl groups is the benzoyl group in which the phenyl group can be substituted once or several times by substituents such as $C_1-C_3$-alkyl, $C_1-C_3$-alkoxy, halogen, nitro, amino, substituted amino, and trifluoromethyl. Examples of aralkanoyl and heteroaroyl groups are phenyl acetyl and pyridine-3-carbonyl groups.

The dialkylaminoalkyl groups are to be understood to be those in which each of the alkyl groups contains 1 to 6 carbon atoms, for example diethylaminoethyl.

If X and Y or $X_1$ and $Y_1$ form, together with the nitrogen atom to which they are bonded, a heterocyclic ring, those which are preferred are piperidine, pyrrolidine, morpholine, piperazine, thiomorpholine, imidazole and theophylline, each of which can optionally be substituted in one or more positions by $C_1-C_4$-alkyl, $C_1-C_4$-alkoxy, aryl, aryl-$C_1-C_4$-alkyl, hydroxyl, amino or substituted $C_1-C_4$-alkyl.

Suitable examples of the salts of the compounds according to the invention with inorganic or organic acids are the hydrochloride, hydrobromide, sulfate, phosphate, acetate, oxalate, tartrate, citrate, maleate or fumarate.

In the formula depicted here, the various substituents are shown as connected to the labdane nucleus in one or two modes of representation: a full line—which indicates a substituent in the β-orientation (i.e. above the plane of the molecule), and a broken line (- - -) which indicates a substituent in the α-orientation (i.e. below the plane of the molecule). All the formulae are drawn in such a way that they depict the compounds in their absolute stereochemical configuration. Where the starting materials having a labdane nucleus are naturally occurring or are derived from natural products they have, as do the final products, a labdane nucleus in the single absolue configuration depicted here. However, the process according to the invention is also meant for the synthesis of labdanes of the racemic series.

In addition to the optical centers of the labdane nucleus, the substituents thereon may also have chiral centers which contribute to the optical properties of the compounds to the invention and allow their separation by conventional methods, for example by the use of optically active acids. A wavy line (~) connecting a group to a chiral center indicates that the stereochemistry of the center is unknown, i.e. the group may be present in either of the possible orientations. This invention embrces all the optical isomers and racemic forms of the compounds according to the invention where such compounds have chiral centers in addition to those of the labdane nucleus.

Some of the new, polyoxygenated labdane derivatives according to the invention are listed in Table 1 which is as follows:

TABLE 1

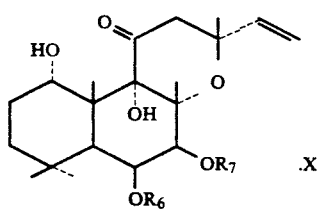

| $R_6$ | $R_7$ | X | Melting point (°C.) |
|---|---|---|---|
| CO(CH$_2$)$_2$—N⟨piperidine⟩ | COCH$_2$OCH$_3$ | HCl | 146–150 |
| CO(CH$_2$)$_2$—N⟨piperidine⟩ | COCH$_2$OC$_2$H$_5$ | HCl | 249–251 |
| CO(CH$_2$)$_2$—N⟨piperidine⟩ | COCH$_2$OC$_6$H$_5$ | HCl | 231–233 |
| CO(CH$_2$)$_2$—N⟨piperidine⟩ | COCH$_2$OC$_6$H$_4$Cl(p) | HCl | 226–228 |
| CO(CH$_2$)$_2$—N⟨morpholine⟩ | COCH$_2$OCH$_3$ | HCl | 160 |
| CO(CH$_2$)$_2$—N⟨morpholine⟩ | COCH$_2$OC$_2$H$_5$ | HCl | 139–141 |
| CO(CH$_2$)$_2$—N⟨morpholine⟩ | COCH$_2$OC$_6$H$_5$ | HCl | 230 |
| CO(CH$_2$)$_2$—N⟨morpholine⟩ | COCH$_2$OC$_6$H$_4$Cl (p) | HCl | 256–257 |
| COCH$_2$CH$_2$—N⟨N-methylpiperazine⟩N—CH$_3$ | COCH$_2$OC$_2$H$_5$ | 2HCl | 215 |
| COCH$_2$CH$_2$—N⟨N-methylpiperazine⟩N—CH$_3$ | COCH$_2$OC$_6$H$_5$ | 2HCl | 207–208 |
| COCH$_2$CH$_2$—N⟨N-methylpiperazine⟩N—CH$_3$ | COCH$_2$OC$_6$H$_4$—Cl (p) | 2HCl | 207–208 |
| COCH$_2$CH$_2$N(CH$_3$)$_2$ | COCH$_2$OCH$_3$ | HCl | 238–237 |
| COCH$_2$CH$_2$N(CH$_3$)$_2$ | COCH$_2$OC$_2$H$_5$ | HCl | 218 |

TABLE 1-continued

[structure shown with HO, OH, OR7, OR6, X substituents]

| R6 | R7 | X | Melting point (°C.) |
|---|---|---|---|
| COCH₂CH₂N(CH₃)₂ | COCH₂OC₆H₅ | HCl | 219 |
| COCH₂CH₂N(CH₃)₂ | COCH₂OC₆H₄—Cl (p) | HCl | 242–243 |
| COCH₂OCH₃ | COCH₂CH₂NMe₂ | HCl | 242–243 |
| COCH₂OCH₃ | COCH₂CH₂N⟨piperidine⟩ | HCl | 215–217 |
| COCH₂OCH₃ | COCH₂CH₂N⟨morpholine⟩ | HCl | 194–196 |
| COCH₂OCH₃ | COCH₂CH₂N⟨N-methylpiperazine⟩ | 2HCl | 206–208 |

The invention also relates to a process for the preparation of the new acyllabdanes of the formula I, which comprises reaction of compounds of the formula II

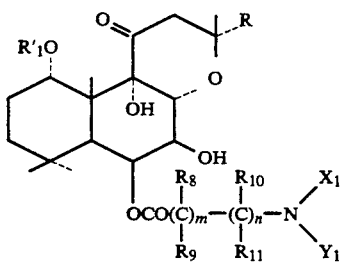

(II)

in which R'₁ denotes a protective group for a hydroxyl group such as the methyl ether, t-butyl ether, allyl ether, benzyl ether, trialkyl-methyl ether, trialkylsilyl ether or tetrahydropyranyl ether or esters, particularly the t-butyldimethylsilyl group and R, R₈–R₁₁ and X₁ and Y₁ have the above-mentioned meanings, with a mixture of an appropriate acid of the formula

B—COOH

[wherein B denotes substituted alkyl,] preferably of the formula R₁₂ZCH₂COOH [wherein Z is oxygen and R₁₂ is alkyl, preferably C₁-C₄-alkyl, or aryl, preferably phenyl, which may be substituted, for example by halogen, or a heterocycle],dicyclohexyl carbodiimide (DCC), and 4-dimethylaminopyridine in organic solvents, such as e.g. dichloro methane, DMF or ethyl acetate, at temperatures in the range of about 20° C. to 70° C., to give compounds of the formula III

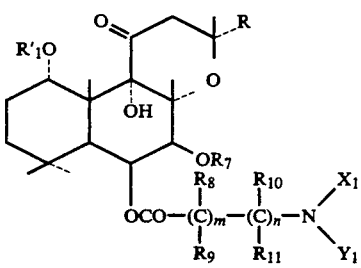

(III)

in which R'₁ represents a protective group, R₇ represents

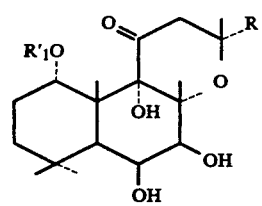

(IV)

in which B denotes substituted alkyl, and R, R₈₋R₁₁, m and n have the above-mentioned meanings. The reaction, product of the formula III is obtained from the mixture by extraction with an organic solvent, washing the organic layer with water, drying it over e.g. anhydrous sodium sulfate and concentrating in vacuo. A chromatographic method may be used for purification, if necessary.

Compounds of the formula III in which R'₁ represents a protective group such as, for example, t-butyl-dimethylsilyl are treated with deprotection reagents such as e.g. tetrabutylammonium fluoride in solvents such as e.g. THF or ether at temperatures in the range of about 0° to 30° C. in order to obtain corresponding compounds of the formula I with R′$_1$ =H.

Compounds of the formula II are prepared by the process which is described in EP-A 0,217,372 and J. Med. Chem. 31, 1872 (1988), from compounds of the formula IV

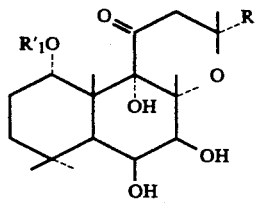

in which R′$_1$ represents a protective group such as t-butyl dimethyl silyl, and R represents a vinyl group.

Compounds of the formula IV are prepared from forskolin (V) by the reaction sequence indicated below:

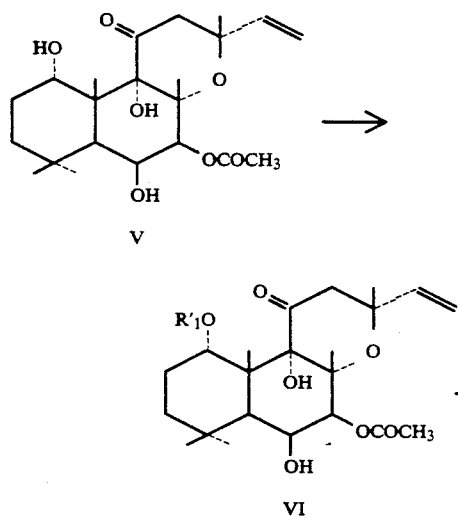

The 1-OH group in forskolin (V) is protected with a group R′$_1$, as defined above, by methods known from the literature (cf. Reagents for Org. Synth., L. F. Fieser and M. Fieser, John Wiley & Sons, Volumes 1 to 11).

The acetyl group in the 7-position in compounds of the formula VI is eliminated by alkaline hydrolysis by methods described in the literature [cf. J.C.S. Perkin I, 769 (1982), and J. Med. Chem. 31, 1872 (1988)], which provides compounds of the formula IV.

Compounds of the formula 1 can also be obtained starting from compounds of the formula IV. Compounds of the formula IV in which R′$_1$ has the above menaing are treated with carboxylic acids of the formula R$_{13}$R$_{14}$C=CH—COOH or R$_{12}$ZCH$_2$COOH in which R$_{12}$—R$_{14}$ represent hydrogen or an alkyl or substituted alkyl or aryl group or substituted aryl or aralkyl, wherein alkyl is preferably C$_1$–C$_4$-alkyl and aryl is preferably phenyl, in the presence of 4-dimethyl amino-pyridine and DCC in organic solvents such as e.g. dry dimethyl formamide or dry ethyl acetate, at temperatures in the range of about 20° to 30° C. for about four hours, and the products of the formula VII

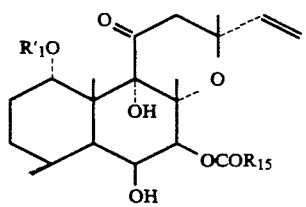

in which R$_{15}$ is

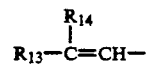

or R$_{12}$OCH$_2$— and R′$_1$ and R$_{12}$-R$_{14}$ have the above meanings, are isolated from the raction mixture by dilution with water, subsequent extraction with organic solvents such as e.g. ethyl acetate, washing of the extract with water, drying over e.g. anhydrous sodium sulfate, and concentration in vacuo. Chromatographic methods are used—if necessary—for purification J. Med. Chem. 31, 1872 (1988).

In order to obtain compounds of the formula VIII

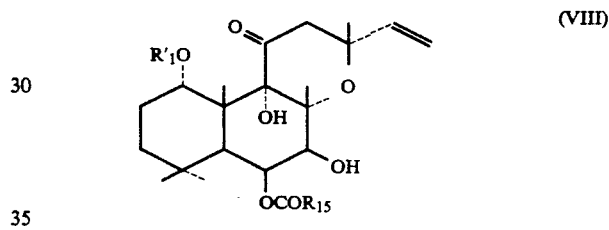

in which R′$_1$, R$_{15}$ have the above meanings, compounds of the formula VII are subsequently treated with alkali such as sodium hydroxide in water-soluble organic solvents such as acetonitrile [J. Med. Chem. 31, 1872 (1988)].

Compounds of the formula VIII are subsequently treated with a substituted organic acid of the formula R$_{16}$COOH, such as e.g. methoxy acetic acid, ethoxy acetic acid, phenoxy acetic acid or p-chlorophenoxy acetic acid, phenyl acetic acid, acrylic acid or substituted acrylic acid in presence of DCC and 4-dimethylamino pyridine in organic solvents such as e.g. dichloromethane, DMF or ethyl acetate, resulting in compounds of the formula IX in which one of R$_{15}$ or R$_{16}$ is R$_{13}$R$_{14}$C=CH— and the other is R$_{12}$OCH$_2$— and wherein R′$_1$ and R$_{12}$-R$_{14}$ have the above meanings.

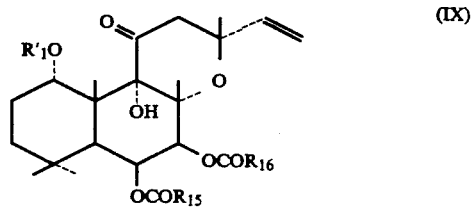

Compounds of the formula IX are treated with the appropriate amine of the formula HNX$_1$Y$_1$, in which X$_1$ and Y$_1$ have the above-mentioned meanings, in an organic solvent such as e.g. dichloromethane, at a temperature of about 20° to 30° C. for about 16 to 24 hours. The product is obtained from the reaction mixture by extraction with an organic solvent, washing of the extract with water, drying over e.g. anhydrous sodium sulfate and concentration in vacuo. The compounds of the formula I which still carry the protective group $R'_1$ are purified—if necessary—by column chromatography. The resulting compounds are deprotected by deprotection reagents such as e.g. tetrabutylammonium fluoride in solvents such as e.g. THF or ether at temperatures in the range of about 0° to 30° C. to give compounds of the formula I wherein $R_1$ is hydrogen.

The compounds according to the invention, and their salts exhibit useful effects on cardiovascular diseases, in particular, a selective positive inotropic effect, and a lowering of the intraocular pressure. This is illustrated by the pharmacological investigations which follow and which were carried out to evaluate the compounds according to the invention, and their salts, and by the results obtained thereby.

POSITIVE INOTROPIC ACTIVITY

The following method was used:

Guinea pigs of both sexes and weighing 400 g are sacrificed, and the heart is removed and placed in Ringer's solution at room temperature. Both the left and the right atria are then isolated, fixed in an organ holder and placed in a bath containing Ringer's solution and maintained at a temperature of 32° C. A mixture of 95% $O_2$ and 5% $CO_2$ is bubbled through the organ bath. Electrical stimulation of the atrium is then carried out. A compound according to the invention is dissolved in water to give a solution of known concentration and is added to the bath. The contractility of the atrium is recorded for 7 to 10 minutes via an isomeric strain gage on a Nihon Kohden 4-channel pen recorder. The activity is expressed on the basis of the resulting data as the $EC_{50}$.

The results obtained in this model for representative compounds according to the invention are listed in the table II. Data for compounds disclosed in Indian Patent No. 163 242 are also provided for comparison.

TABLE II

| $R_6$ | $R_7$ | Guinea pig atrium $EC_{50}$ g/ml |
|---|---|---|
|  | $COCH_2OC_2H_5$ | 0.044 |
| $^aCO(CH_2)_2N\diagup\diagdown O$.HCl |  |  |
| $^aCO(CH_2)_2 N(CH_3)_2$.2HCl | $COCH_2OCH_3$ | 0.024 |
| $^aCOCH_2OCH_3$ | $CO(CH_2)_2NMe_2$.HCl | 0.77 |
|  | H | Not active |
| $^bCO(CH_2)_2N\diagup\diagdown O$.HCl |  |  |
| $^bCOCH_2N\diagup\diagdown$.HCl | H | 1.8 |

$^a$Compounds of instant invention,
$^b$Compounds of Indian Patent No. 163242.

Measurement of the intraocular pressure in conscious rabbits

For this experiment rabbits of both sexes and weighin 2 to 3 kg are used. The intraocular pressure (IOP) is measured with a Schioetz tonometer after corneal anaesthesia with a 2% novocaine solution. A 2% solution of a compound according to the invention is prepared, using the stoichiometric amount of 0.1N HCl, by dissolving it or its salt directly in water. After the initial value has been determined, 100 μl of the solution of the test compound are distilled into one of the eyes, and the vehicle is instilled into the other eye. The IOP is measured at defined time intervals, i.e. 0.5, 1, 2, 3, 4 and 5 hours. The percentage decreases in the IOP is calculated using the initial value.

The results obtained in this model for representative compounds according to the invention are listed in the table III

TABLE III

| Compound $R_6$ | $R_7$ | Dose percentage | IOP-Lowering Effect % decrease in IOP | Duration |
|---|---|---|---|---|
| $^aCO(CH_2)_2N\diagup\diagdown$.HCl | $COCH_2OPh$ | 2 | 31 | 300 |

TABLE III-continued

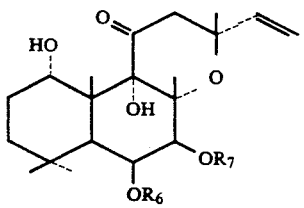

| Compound R₆ | R₇ | Dose percentage | IOP-Lowering Effect % decrease in IOP | Duration |
|---|---|---|---|---|
| ᵃCO(CH₂)₂N⟨O⟩.HCl | COCH₂OEt | 2 | 31 | >360 |
| ᵃCO(CH₂)₂N⟨N—CH₃⟩.2HCl | COCH₂OEt | 2 | 32 | >360 |
| ᵇCOCH₂N⟨ ⟩.HCl | H | 2 | Not active | |

ᵃCompounds of instant invention,
ᵇCompound from Indian Patent No. 163242.

The invention is illustrated by the examples which follow:

EXAMPLE 1

6β-Acryloyloxy-1α-t-butyldimethylsilyloxy-8,13-epoxy-9α-hydroxy-7β-methoxyacetoxy-labd-14-en-11-one Methoxyacetic acid (0.53 ml, 6.92 mmol) was added to a mixture of dicyclo hexylcarbodiimide (1.43 g, 6.92 mmol) and 4-dimethylamino pyridine (0.31 g, 2.54 mmol) in dry ethyl acetate (30 ml). The reaction mixture was stirred for 10 minutes at room temperature. 6β-acryloyloxy-1α-t-butyldimethylsilyloxy-7β, 9α-dihydroxy-8,13 epoxy-labd-14-en-11-one (1.27 g, 2.31 mmol) was added and stirred for 2 hours. The excess dicyclohexylcarbodiimide in the reaction mixture was destroyed by adding water (5 ml). The stirring was continued at room temperature for 10 mins, and the mixture was subsequently filtered. The filtrate was washed with common salt solution. The organic layer was dried over anhydrous sodium sulphate and evaporated. The residue was purified by flash chromatography using ethyl acetate, petroleum ether (75:92.5) as eluant. Yield 90%, m.p. 144°-145° C.

Similarly, following compounds were prepared:

6β-Acryloyloxy-1α-t-butyldimethylsilyloxy-8,13-epoxy-7β-ethoxy-acetoxy-9α-hydroxylabd-14 -en-11-one, m.p. 120°-121° C.
6β-Acryloyloxy-1α-t-butyldimethylsilyloxy-8,13-epoxy-9α-hydroxy-7β-phenylacetoxy-labd-14 -en-11-one, m.p. 122°-123° C.
6β-Acryloyloxy-1α-t-butyldimethylsilyloxy-8,13-epoxy-9α-hydroxy-7β-phenoxyacetoxy-labd-14 -en-11-one, m.p. 140° C.
6β-Acryloyloxy-1α-t-butyldimethylsilyloxy-8,13-epoxy-7β-( p-chlorophenoxy)-acetoxy-9α-hydroxylabd-14-en-11one, m.p. 168°-169° C.
7β-Acryloyloxy-1α-t-butyldimethylsilyloxy-8,13-epoxy-9α-hydroxy-6β-methoxyacetoxy-labd-14-en-11-one, m.p. 149° C.
1α-t-butyldimethylsilyloxy-6β,9α-dihydroxy-8,13-epoxy-7β-methoxy-acetoxy-labd-14-en-11-one.

EXAMPLE 2

6β-Acryloyloxy-1α,9α-dihydroxy-8,13-epoxy-7β-methoxyacetoxy-labd-14-en-11-one

6β-Acryloyloxy-1α-t-butyldimethylsilyloxy-8,13-epoxy-9α-hydroxy-7β-methoxyacetoxy-labd-14-en-11-one (1.38 g, 2.28 mmol) in anhydrous tetrahydrofuran (30 ml) was stirred with tetrabutyl ammonium fluoride trihydrate (0.81 g, 2.51 mmol) for half an hour at room temperature and the reaction mixture was concentrated. The residue was extracted with ethyl acetate, the organic layer was washed with brine solution, dried over anhydrous sodium sulphate and concentrated. The residue obtained was purified by flash chromatography using ethyl acetate:petroleum ether (1:4) as eluant. The compound was used as such for the next step. Yield 77%, m.p. 176°-178° C.

Similarly following compounds were prepared:

6β-Acryloyloxy-1α,9α-dihydroxy-8,13-epoxy-7β-ethoxyacetoxy-labd-14-en-11-one, m.p. 157°-158° C.
7β-Acryloyloxy-1α,9α-dihydroxy-8,13-epoxy-6β-methoxyacetoxy-labd-14-en.11-one, m.p. 194°-195° C.

EXAMPLE 3

1α,9α-Dihydroxy-6β-(3-N,N-dimethylamino-propionyloxy)-8,13-epoxy-7β-methoxy-acetoxy-labd-14-en-11-one 6β-Acryloyloxy-1α,9α-dihydroxy-8,13-epoxy-7β-methoxyacetoxy-labd-14-en-11-one (0.225 g, 0.47 mmol) was dissolved in dimethylamine in toluene (15 ml) and kept at 30° C. in a pressure vessel overnight. The reaction mixture was concentrated in vacuo. The residue was purified by flash chromatography on silica gel using ethyl acetate:petroleum ether:triethylamine (80:19:1) as eluant. Yield 40%, m.p. 169°-171° C.

Similarly, following compounds were prepared.

1α,9α-Dihydroxy-8,13-epoxy-6β-(3-N,N-dimethylamino-propionyloxy)-7β-ethoxyacetoxy-labd-14-en-11-one, m.p. 146°-147° C.

1α,9α-Dihydroxy-7β-(3-N,N-dimethylamino-propionyloxy)-8,13- epoxy-6β-methoxyacetoxy-labd-14-en-11-one, m.p. 183°-184° C.

1α,9α-Dihydroxy-8,13-epoxy-6β-methoxyacetoxy-7β-(3-piperidino-propionyloxy)-labd-14-en-11-one, m.p. 209°-210° C.

1α,9α-Dihydroxy-8,13-epoxy-6β-methoxyacetoxy-7β-(3-morpholino-propionyloxy)-labd-14-en-11-one, m.p. 205°-206° C.

1α,9α-Dihydroxy-8,13-epoxy-6β-methoxyacetoxy-7β-(3-N-methylpiperazino-propionyloxy)-labd-14-en-11-one, m.p. 200°-201° C.

EXAMPLE 4

1α,9α-Dihydroxy-8,13-epoxy-7β-methoxyacetoxy-6β-(3-piperdidino-propionyloxy)-labd-14-en-11-one Piperidine (1 ml) was added to a stirred solution of 6β-acryloyloxy-1α,9α-dihydroxy-8,13-7β-methoxyacetoxy-labd-14-en-11-one (0.25 g, 0.506 mmol) in methylene chloride (10 ml). Stirring was continued overnight. The reaction mixture was concentrated under vacuo and the residue was purified by flash column chromatography using ethyl acetate:petroleum ether: triethylamine (40:59:1) as eluant. Compound was recrystallised from ethyl acetate:petroleum ether. Yield 70%, m.p. 136°-137° C.

Similarly following compounds were prepared:

1α,9α-Dihydroxy-8,13-epoxy-7β-methoxyacetoxy-6β-(3-morpholino-propionyloxy)-labd-14-en-11-one, m.p. 132°-133° C.

1α,9α-Dihydroxy-8,13-epoxy-7β-methoxyacetoxy-6β-(3-N-methyl-piperiazino-propionyloxy)-labd-14-en-11-one, m.p.

1α,9α-Dihydroxy-8,13-epoxy-7β-ethoxyacetoxy-6β-(3-piperidino-propionyloxy)-labd-14-en-11-one, m.p. 113°-114° C.

1α,9α-Dihydroxy-8,13-epoxy-7β-ethoxyacetoxy-6β-(3-morpholino-propionyloxy)-labd-14-en-11 -one, m.p. 123°-124° C.

1α,9α-Dihydroxy-8,13-epoxy-7β-ethoxyacetoxy-6β-(3-N-methyl-piperazino-propionyloxy)-labd-14 -en-11-one, m.p. 163°-164° C.

1α,9α-Dihydroxy-8,13-epoxy-7β-phenoxyacetoxy-6β-(3-piperidino-propionyloxy)-labd-14-en-11-one, m.p. 140°-141° C.

1α,9α-Dihydroxy-8,13-epoxy-7β-phenoxyacetoxy-6β-(3- morpholino-propionyloxy)-labd-14-en-11-one, m.p. 157°-158° C.

1α,9α-Dihydroxy-8,13-epoxy-7β-phenoxyacetoxy-6β-(3-N-methyl-piperazino-propionyloxy)-labd-14 -en-11-one, m.p. 183°-184° C.

7β-p-chlorophenoxyacetoxy-1α,9α-dihydroxy-8,13-epoxy-6β-(3-piperidino-propionyloxy)-labd-14-en-11-one, m.p. 151° C.

7β-p-chlorophenoxyacetoxy-1α,9α-dihydroxy-8,13-epoxy-6β-(3-morpholino-propionyloxy)-labd-14-en-11-one, m.p. 151° C.

7β-p-chlorophenoxyacetoxy-1α,9α-dihydroxy-8,13-epoxy-6β-(3-N-methyl-piperazinopropionyloxy)-labd-14-en-11-one, m.p. 203°-204° C.

Following compounds were prepared by using anhydrous dimethylamine in toiluene in place of piperidine:

1α,9α-Dihydroxy-6β-(3-N,N-dimethylaminopropionyloxy)-8,13-epoxy-7β-methoxyacetoxy-labd-14-en-11-one, m.p. 169°-171° C.

1α,9α-Dihydroxy-6β-(3-N,N-dimethylaminopropionyloxy)-8,13epoxy-7β-ethoxyacetoxy-labd-14-en-11-one, m.p. 146°-147° C.

1α,9α-Dihydroxy 6β-(3-N,N-dimethylamino-propionyloxy)-8,13-epoxy-7β-phenoxyacetoxy-labd-14-en-11-one, m.p. 184°-185° C.

7β-p-Chlorophenoxyacetoxy-1α,9α-dihydroxy-6β-(3-N,N-dimethylaminopropionyloxy)-8,13-epoxy-labd-14-en-11-one, m.p. 153°-154° C.

EXAMPLE 5

1α-t-Butyldimethylsilyloxy-7β,9α-dihydroxy-8,13-epoxy-6β-methoxyacetoxy-labd-14-en-11-one 1α-t-Butyldimethylsilyloxy-6β,9α-dihydroxy-8,13-epoxy-7β-methoxyacetoxy-labd-14-en-11-one (12.3 g, 22.2 mmol) was added to a stirred mixture of acetonitrile (660 ml), water (540 ml) and potassium carbonate (3.37 g, 24.42 mmol) at room temperature. Stirring was continued for 4 hours. The reaction mixture was concentrated at low temperature (30°-35° C.) in vacuo. The residual mixture was extracted with ethyl acetate. The organic layer was Washed with water followed by brine, dried over anhyd. sodium sulphate and concentrated. The residue was purified by chromatography over silica gel using ethyl acetate:diisopropyl ether: petroleum ether (1:1:3) as eluant yield 8.3 g.

EXAMPLE 6

General Method for Preparation of Hydrochloride Salts

Diethyl ether saturated with dry HCl gas was added to the methanolic solution of the compound (prepared in Example3 and 4) at 0° C. The reaction mixture was further diluted with diethyl ether and filtered. The precipitate thus obtained was filtered and crystallized with methanol:diethyl ether and gave the corresponding hydrochloride salts (listed in Table I).

We claim:

1. A compound having the formula

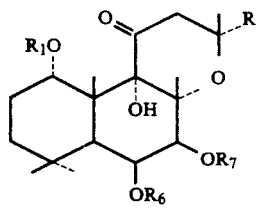

wherein
R is vinyl;
$R_1$ is hydrogen;
$R_6$ is $-CO(CH_2)_2NX_1Y_1$, wherein $X_1$ and $Y_1$ are each methyl or $X_1$ and $Y_1$ form, together with the N atom to which they are bonded, a piperidine, morpholine, or N-methylpiperazine ring; and
$R_7$ is $-COCH_2OZ_1$, wherein $Z_1$ is methyl, ethyl, phenyl, or 4-chlorophenyl;
and the optical and geometric isomers and pharmaceutically acceptable salts thereof.

2. A compound having the formula

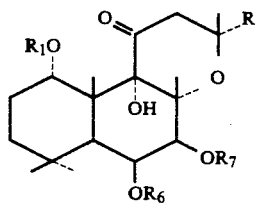

wherein
R is vinyl;
$R_1$ is hydrogen;
$R_6$ is $-COCH_2OCH_3$; and
$R_7$ is $-CO(CH_2)_2NX_1Y_1$, wherein $X_1$ and $Y_1$ are each methyl or $X_1$ and $Y_1$ form, together with the N atom to which they are bonded, a piperidine, morpholine, or N-methylpiperazine ring;
and the optical and geometric isomers and pharmaceutically acceptable salts thereof.

3. Process for the manufacture of a compound as claimed in claim 1, which comprises splitting off the protective group $R'_1$ from compounds of the formula

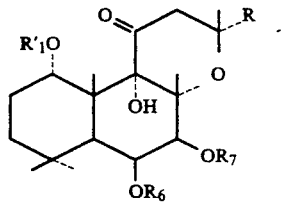

and the optical and geometric isomers and pharmaceutically acceptable salts thereof.

4. Process for the manufacture of a compound as claimed in claim 2, which comprises splitting off the protective group $R'_1$ from compounds of the formula

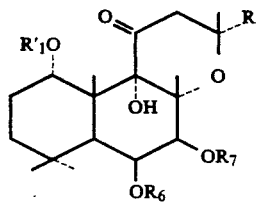

and the optical and geometric isomers and pharmaceutically acceptable salts thereof.

5. A method of treating cardiovascular diseases selected from the group consisting of congestive cardiomyopathy, hypertension, and thrombosis, which comprises administering to a host in need thereof a compound according to claim 1 in an amount effective to treat cardiovascular diseases.

6. A method of treating cardiovascular diseases selected from the group consisting of congestive cardiomyopathy, hypertension, and thrombosis, which comprises administering to a host in need thereof a compound according to claim 2 in an amount effective to treat cardiovascular diseases.

7. A method of lowering intraocular pressure, which comprises administering to a host in need thereof a compound according to claim 1 in an amount effective to lower intraocular pressure.

8. A method of lowering intraocular pressure, which comprises administering to a host in need thereof a compound according to claim 2 in an amount effective to lower intraocular pressure.

* * * * *

UNITED STATES PATENT AND TRADEMARK OFFICE
CERTIFICATE OF CORRECTION

PATENT NO. : 5,206,241
DATED : April 27, 1993
INVENTOR(S) : Yatendra Khandelwal et al.

It is certified that error appears in the above-indentified patent and that said Letters Patent is hereby corrected as shown below:

Title page, item [75], line 3, under Inventors, after "Vijay A. Aroskar", insert --, all of Bombay, India--.

Item [75], lines 4-7, should read --AliHussein N. Dohadwalla, deceased, late of Bombay, India, by Rashida A. Dohadwalla, Anis AliHussein Dohadwalla, and Samina A. Dohadwalla, All of Bombay, India, heirs; Richard--.

Signed and Sealed this

Nineteenth Day of July, 1994

Attest:

BRUCE LEHMAN

Attesting Officer

Commissioner of Patents and Trademarks